(12) United States Patent
Flanagan et al.

(10) Patent No.: US 8,361,139 B2
(45) Date of Patent: Jan. 29, 2013

(54) MEDICAL DEVICES HAVING METAL COATINGS FOR CONTROLLED DRUG RELEASE

(75) Inventors: Aiden Flanagan, Kilcolgan (IE); Barry O'Brien, Galway (IE); Torsten Scheuermann, Munich (DE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 654 days.

(21) Appl. No.: 12/498,829

(22) Filed: Jul. 7, 2009

(65) Prior Publication Data

US 2010/0015206 A1    Jan. 21, 2010

Related U.S. Application Data

(60) Provisional application No. 61/081,203, filed on Jul. 16, 2008.

(51) Int. Cl.
*A61F 2/06* (2006.01)
*A61F 2/00* (2006.01)

(52) U.S. Cl. ........ 623/1.15; 424/423; 424/426; 424/428

(58) Field of Classification Search .................. None
See application file for complete search history.

(56) References Cited

U.S. PATENT DOCUMENTS

| | | | |
|---|---|---|---|
| 4,321,311 A | 3/1982 | Strangman | |
| 5,874,134 A | 2/1999 | Rao et al. | |
| 6,180,184 B1 | 1/2001 | Gray et al. | |
| 6,663,662 B2 | 12/2003 | Pacetti et al. | |
| 6,716,444 B1 | 4/2004 | Castro et al. | |
| 6,924,004 B2 | 8/2005 | Rao et al. | |
| 2003/0125803 A1* | 7/2003 | Vallana et al. | 623/1.42 |
| 2007/0038176 A1 | 2/2007 | Weber et al. | |
| 2007/0156231 A1 | 7/2007 | Weber | |

FOREIGN PATENT DOCUMENTS

| | | |
|---|---|---|
| WO | 03/047636 | 6/2003 |
| WO | 03/045582 | 6/2006 |
| WO | 2007/034167 A2 | 3/2007 |
| WO | 2009/079389 | 6/2009 |

OTHER PUBLICATIONS

International Preliminary Report on Patentability issued by the WIPO on Jan. 27, 2011, for PCT application: PCT/US2009/049802 filed on Jul. 7, 2009.
L. Hakim et al., "Nanocoating Individual Silica Nanoparticles by Atomic Layer Deposition in a Fluidized Bed Reactor," Chem. Vap. Deposition, vol. 11, pp. 420-425 (2005).

* cited by examiner

*Primary Examiner* — Robert A Wax
*Assistant Examiner* — Tigabu Kassa
(74) *Attorney, Agent, or Firm* — Fish & Richardson P.C.

(57) ABSTRACT

Medical devices having a plurality of nanoparticles disposed over a surface of the medical device. The nanoparticles have a core comprising a therapeutic agent and a shell surrounding the core, wherein the shell comprises a metal. A barrier layer is disposed over the nanoparticles. The barrier layer is water-permeable and comprises a metal that may be different from the metal used in the nanoparticle shells. In certain embodiments, the metal in the barrier layer undergoes galvanic corrosion. Also disclosed are medical device having a reservoir containing a therapeutic agent, with nanoparticles and a barrier layer being disposed over the reservoir; and medical devices having multiple barrier layers and multiple reservoirs containing therapeutic agents.

14 Claims, 3 Drawing Sheets

MEDICAL DEVICES HAVING METAL COATINGS FOR CONTROLLED DRUG RELEASE

CROSS REFERENCE TO RELATED APPLICATION

The present application claims priority to U.S. provisional application Ser. No. 61/081,203 filed Jul. 16, 2008, the disclosure of which is incorporated herein by reference in its entirety.

TECHNICAL FIELD

The present invention relates to medical devices, and in particular, medical devices having a coating for controlled release of a therapeutic agent.

BACKGROUND

Many implantable medical devices are coated with drugs that are eluted from the medical device upon implantation. For example, some vascular stents are coated with a drug which is eluted from the stent for treatment of the vessel and/or to prevent some of the unwanted effects and complications of implanting the stent. In such drug-eluting medical devices, various methods have been proposed to provide a mechanism for drug elution. However, there is a continuing desire for improved devices and methods for providing drug elution from medical devices.

SUMMARY

In one aspect, the present invention provides a medical device comprising: a plurality of nanoparticles disposed over a surface of the medical device, wherein each nanoparticle comprises: (a) a core containing a therapeutic agent; and (b) a shell surrounding the core, wherein the shell comprises a first metal; and a barrier layer disposed over the plurality of nanoparticles, wherein the barrier layer comprises a second metal; wherein the first metal and the second metal are different, and wherein the first metal and the second metals have different electronegativities.

In another aspect, the present invention provides a medical device comprising: a reservoir containing a first therapeutic agent; a plurality of nanoparticles disposed over the reservoir, wherein each nanoparticle comprises: (a) a core containing a second therapeutic agent; and (b) a shell surrounding the core, wherein the shell comprises a first metal; and a barrier layer disposed over the nanoparticles and the reservoir, wherein the barrier layer comprises a second metal.

In yet another aspect, the present invention provides a medical device comprising: a first reservoir containing a first therapeutic agent; a first barrier layer disposed over the first reservoir, wherein the first barrier layer comprises a first metal; a second reservoir disposed over the first barrier layer, wherein the second reservoir contains a second therapeutic agent; and a second barrier layer disposed over the second reservoir, wherein the second barrier layer comprises a second metal.

BRIEF DESCRIPTION OF THE DRAWINGS

FIG. 1A shows a close-up, cross-sectional view of the nanoparticle. FIG. 1B shows a cross-sectional view of the strut portion with the nanoparticles disposed thereon and a barrier layer covering the nanoparticles. FIG. 1C shows the strut portion with the barrier layer in an eroded condition.

FIG. 2A shows a close-up, cross-sectional view of the nanoparticle. FIG. 2B shows a cross-sectional view of the strut portion with the nanoparticles, a barrier layer, an intervening layer, and a reservoir layer containing a therapeutic agent. FIG. 2C shows a close-up view of the nanoparticle within the barrier layer with the nanoparticle shell in an eroded condition. FIG. 2D shows the strut portion with the barrier layer eroded away and the intervening layer in an eroded condition.

FIG. 3A shows the strut portion with the outer barrier layer and the inner barrier layer intact. FIG. 3B shows the strut portion with the outer barrier layer in an eroded condition. FIG. 3C shows the strut portion with the outer barrier layer eroded away. FIG. 3D shows the strut portion with the inner barrier layer in an eroded condition.

DETAILED DESCRIPTION

Figure 1A:
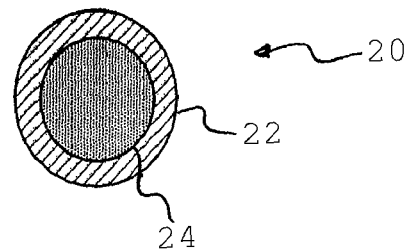
FIGS. 1A-1C show nanoparticles and strut portions of a stent according to an embodiment of the present invention.

The present invention provides various medical devices having a coating for controlled release of therapeutic agents. In one aspect, the present invention provides a medical device comprising a plurality of nanoparticles disposed over a surface of the medical device. The nanoparticles have a core comprising a first therapeutic agent and a shell surrounding the core, wherein the shell comprises a first metal. The core can be formed using any of various methods known in the art for making therapeutic agents in particulate form. For example, a fine nanoparticulate powder of the therapeutic agent can be formed by wet bead milling, high pressure homogenization (e.g., a suspension of a drug is forced to pass through a narrow orifice under high pressure), use of supercritical fluid technology, use of fluidized bed technology, or use of spray-drying technology. The core may also include other pharmaceutically-acceptable excipients, such as plasticizers, binders, fillers, surfactants, etc.

The shell can be formed around the core using any of the various thin-film deposition techniques for use with inorganic materials, including chemical or physical vapor deposition, atomic layer deposition, evaporation, pulsed laser deposition, etc. For example, the shell may be formed by a process similar to that reported by L. Hakim et al., "Nanocoating Individual Silica Nanoparticles by Atomic Layer Deposition in a Fluidized Bed Reactor," *Chem. Vap. Deposition*, vol. 11, pp. 420-425 (2005), in which silica nanoparticles of 40 nm size were individually and conformally coated with alumina films using atomic layer deposition (ALD) in a fluidized bed reactor.

The nanoparticles of the present invention can be applied to the medical device using any of the various methods by which fine particulate materials are deposited onto a substrate. For example, a colloidal suspension of the nanoparticles can be formed and the colloidal suspension applied onto the medical device (e.g., by dipping, spraying, or roll-coating using the colloidal suspension). After drying of the suspension liquid, the nanoparticles remain on the medical device. In another example, the method described in WO 2007/034167 (Mantis Deposition, Ltd.) could be adapted to deposit nanoparticles of the present invention onto the medical device (e.g., by electrostatic acceleration of the therapeutic agent-containing nanoparticles).

The medical device may further comprise a barrier layer disposed over the nanoparticles. Where a barrier layer is described as being "disposed over" another element, at least a portion of the barrier layer is disposed further away from the surface of the medical device than the other element. As such, in this case, the barrier layer being disposed over the nanoparticles includes the barrier layer covering the nanoparticles (whether or not the nanoparticles are in direct contact with the barrier layer) and/or having the nanoparticles contained within the barrier layer.

The thickness of the barrier layer will depend upon the particular application. In some cases, the thickness of the barrier layer is in the range of 100 nm to 10 µm; and in some cases, 1 µm or less (e.g., in the range of 100 nm to 1 µm).

The barrier layer comprises a second metal and is water-permeable. The nanoparticles are retained on the medical device by being contained within the barrier layer and/or being covered by the barrier layer. After implantation in the body, the barrier layer is designed to undergo erosion such that the nanoparticles are released from the medical device. The barrier layer may be formed over the nanoparticles using any of the various layer deposition processes used for inorganic materials, such as vapor deposition, pulsed laser deposition, or high-speed impaction of nanoparticulate materials (as described above).

Depending upon the particular application, the first and second metals may be any of the various metals that are suitable for use in the human body, including iron, magnesium, zinc, aluminum, gold, silver, titanium, manganese, iridium, or alloys of such metals. In some cases, the metals may be selected from those that are biodegradable or bioresorbable, such as iron, magnesium, zinc, or alloys of such metals. The first metal is different from the second metal, and as such, have different electronegative potentials. In certain embodiments, the first metal in the nanoparticle shell and the second metal in the barrier layer are in electrical connectivity; and have an electronegative potential difference that is sufficiently high for a galvanic current to be generated when the medical device is exposed to a physiologic environment (e.g., body fluids containing electrolytes). Electrical connectivity between the first and second metals may be a result of direct contact of the two metals or from the presence of an electrically conductive pathway between the two metals.

In certain embodiments, the second metal in the barrier layer has a lesser electronegative potential than the first metal in the nanoparticle shells. For example, the second metal may be zinc or magnesium and the first metal may be iron. When the medical device is exposed to a physiologic environment, because of its lesser electronegativity, the second metal serves as the anode and undergoes galvanic corrosion. This galvanic corrosion of the second metal facilitates the erosion of the barrier layer. In addition to galvanic corrosion, the barrier layer may also undergo erosion as a result of biodegradative or bioresorptive processes, which may include physical processes, such as the frictional or mechanical forces created by the flow of fluid or blood. The biodegradation process may also includes chemical process, such as corrosion, oxidation, or hydrolysis.

The erosion rate of the barrier layer will depend upon various factors, including its composition, thickness, porosity, electrochemical properties, or mechanical properties. As such, these factors can be adjusted to achieve the desired erosion rate of the barrier layer. In some cases, the barrier layer is designed to erode over a period of less than 2 months; and in some cases, over a period of 2-6 months; and in some cases, over a period of greater than 6 months.

As the barrier layer erodes, it loses its ability to retain the nanoparticles. As such, the nanoparticles are released from the medical device as the barrier layer erodes over time. The released nanoparticles can then be distributed to body tissue (e.g., the nanoparticles can penetrate into or be taken up by body tissue cells). In body tissue, the nanoparticle shells undergo erosion by biodegradative or bioresorptive processes. As the shell erodes, the therapeutic agent contained in the core of the nanoparticle is released.

The medical device may also have other coating layers, such as other layers of inorganic or polymeric materials, which are disposed over or under the barrier layer and/or nanoparticles. The body of the medical device may comprise any of the various materials that can be used in medical devices. In some cases, the body of the medical device comprises the same metal as the barrier layer or the nanoparticle shell.

Figure 1B:
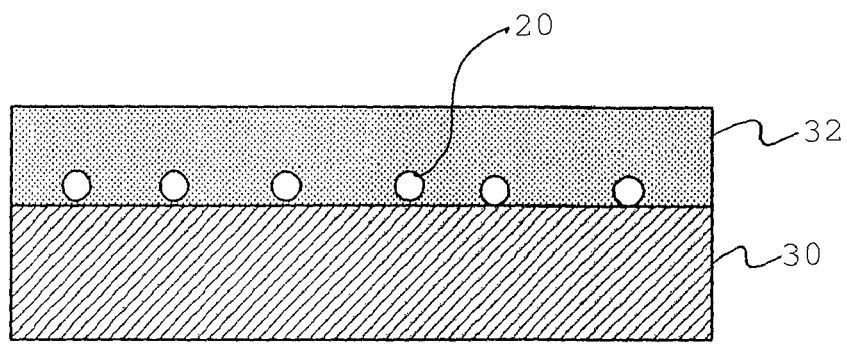
Figure 1C:
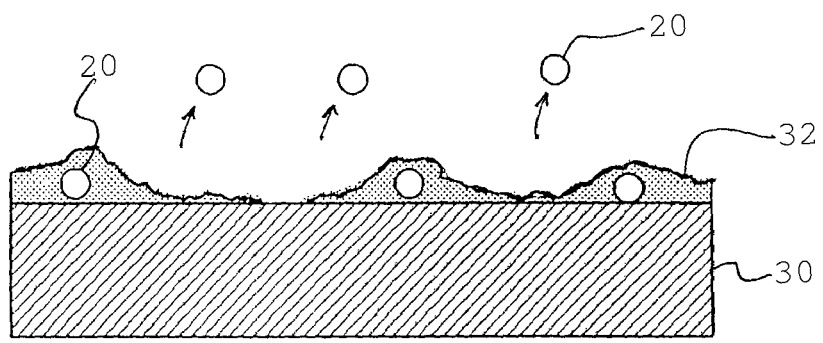

For example, referring to the embodiment shown in FIGS. 1A-1C, a strut portion 30 of a stent is coated with a water-permeable barrier layer 32 (having a thickness of 1 µm or less) formed of magnesium or zinc. A plurality of nanoparticles 20 are covered by barrier layer 32, and as such, nanoparticles 20 are retained on strut portion 30 by barrier layer 32. As shown in FIG. 1A, each nanoparticle 20 comprises a core 24 and a shell 22. Core 24 contains a therapeutic agent (e.g., paclitaxel) and shell 22 is formed of iron. The metal (magnesium or zinc) used in barrier layer 32 is less electronegative than the metal (iron) used in shell 22. The metal in barrier layer 32 is in direct contact with the metal in shell 22 of nanoparticle 20.

In operation, the stent is implanted into a blood vessel. Body fluids (e.g., blood or plasma) penetrate through water-permeable barrier layer 32 and come into contact with the metal in nanoparticles shells 22 and the metal in barrier layer 32. Because of the electrolytes in the body fluids, a galvanic current forms between the metal in shell 22 and the metal in barrier layer 32. As shown in FIG. 1C, this galvanic current facilitates the erosion of barrier layer 32. Erosion of barrier layer 32 allows the release of nanoparticles 20 into the external environment, where they penetrate into or are taken up body tissue. Inside body tissue, nanoparticle shells 22 are degraded by biodegradative or bioresorptive processes, allowing the release of the therapeutic agent contained in core 24.

It will be appreciated that the above-described embodiments have numerous advantages. For example, such embodiments can be used to provide delayed long-term elution of therapeutic agents deep within tissues and cells. For example, in certain embodiments, the therapeutic agent in the core is not released until the nanoparticles are absorbed into tissues or cells. In the case of vascular stents, it can also be advantageous in certain applications to delay release of the therapeutic agent until the nanoparticles are absorbed into a vessel wall or surrounding smooth muscle cells. In another example, the delayed release of the therapeutic agent may be used to confine a cytotoxic agent (e.g., a chemotherapeutic agent) deep within a tumor so as to minimize adverse effects from the distribution of the cytotoxic agent to other parts of the body.

In another aspect, the present invention provides a medical device comprising a reservoir containing a first therapeutic agent. A plurality of nanoparticles are disposed over the reservoir. Where nanoparticles are described as being "disposed over" another element, the nanoparticles are disposed further away from the surface of the medical device than at least a portion of the other element. As described above, the nanoparticles have a core and a shell surrounding the core. The core comprises a second therapeutic agent and the shell comprises a first metal. The first and second therapeutic agents may be the same or different. A barrier layer is disposed over the nanoparticles, wherein the barrier layer comprises a second metal.

The reservoir containing the first therapeutic agent may be provided in any of various ways. The reservoir may be the therapeutic agent formulation alone, or may comprise any structure that retains or holds the therapeutic agent. For example, the reservoir may be a polymer layer or other type of layer over the medical device, with the therapeutic agent disposed therein. In another example, the reservoir may be created in a surface of the medical device (e.g., a porous surface), or the surface may have pits, pores, cavities, or holes that contain the therapeutic agent.

The nanoparticles are retained on the medical device by the nanoparticles being contained within the barrier layer and/or being covered by the barrier layer. After implantation in the body, the nanoparticle shells and the barrier layer are both designed to undergo erosion to control the release of the first and second therapeutic agents, with the nanoparticle shell eroding before the barrier layer erodes.

The nanoparticles may be disposed over the reservoir in various ways. In some cases, the nanoparticles are disposed directly on the reservoir. In some cases, the nanoparticles are disposed on an intervening layer that itself is disposed between the barrier layer and the reservoir (e.g., the intervening layer covers the reservoir, the nanoparticles are disposed on the intervening layer, and the barrier layer covers the nanoparticles and the intervening layer). The intervening layer may be made of a material that is the same or different from the material used in the barrier layer. The intervening layer may be water-permeable or impermeable.

The thickness of the intervening layer will depend upon the particular application. In some cases, the thickness of the intervening layer is in the range of 100 nm to 10 µm; and in some cases, 1 µm or less (e.g., in the range of 100 nm to 1 µm).

The barrier layer is water-permeable, but is able to retain the reservoir and the nanoparticles on the medical device. As described above, the first and second metals may be any of the various metals that are suitable for use in the human body, with the first metal being different from the second metal. In certain embodiments, the first metal in the shell and the second metal in the barrier layer are in electrical connectivity; and have an electronegative potential difference that is sufficiently high for a galvanic current to be generated when the medical device is exposed to a physiologic environment (e.g., blood or body fluids containing electrolytes).

In certain embodiments, the first metal in the nanoparticle shell has a lesser electronegative potential than the second metal in the barrier layer. When the medical device is exposed to a physiologic environment, because of its lesser electronegative potential, the first metal undergoes galvanic corrosion. This galvanic corrosion of the first metal facilitates the erosion of the nanoparticle shells. In addition to galvanic corrosion, the nanoparticle shells may also undergo erosion as a result of biodegradative or bioresorptive processes. As the nanoparticle shells erode, the second therapeutic agent in the nanoparticle cores is released. The second therapeutic agent travels through the water-permeable barrier layer and is released into the external environment.

Over a longer time frame than the erosion of the nanoparticle shell, the barrier layer undergoes erosion through a biodegradation or bioresorption process. As the barrier layer erodes, the reservoir becomes exposed, allowing the first therapeutic agent in the reservoir to be released. The erosion rates of the nanoparticle shells and the barrier layer will depend upon various factors, including their composition, thickness, porosity, electrochemical properties, or mechanical properties. As such, these factors can be adjusted to achieve the desired erosion rates of the nanoparticle shells and the barrier layer.

In some cases, the nanoparticle shells are designed to erode over a period of less than 2 months; and in some cases, over a period of 2-6 months; and in some cases, over a period of greater than 6 months. In some cases, the barrier layer is designed to erode over a period of greater than 6 months; and in some cases, over a period of greater than one year. In some cases, the nanoparticles shells are designed to provide a burst release of the second therapeutic agent (in the nanoparticle cores) and the barrier layer is designed to provide a sustained release of the first therapeutic agent (in the reservoir).

Figure 2A:
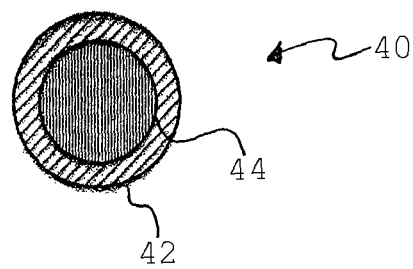
FIGS. 2A-2D show nanoparticles and strut portions of a stent according to another embodiment.
Figure 2B:
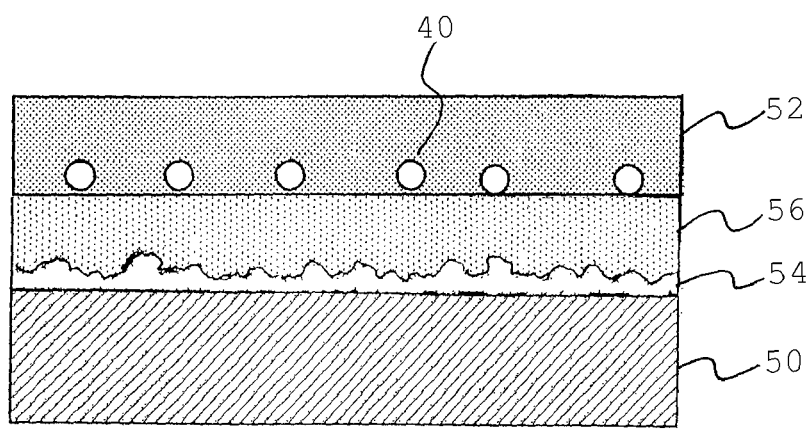

For example, referring to the embodiment shown in FIGS. 2A-2D, a strut portion 50 of a stent is coated with a reservoir layer 54 of a first therapeutic agent (e.g., paclitaxel) in powder form. A non-permeable intervening layer 56 (having a thickness of 1 µm or less) formed of zinc or iron is deposited onto reservoir layer 54 by a layer deposition process. A plurality of nanoparticles 40 are then deposited onto intervening layer 56. As shown in FIG. 2A, each of nanoparticles 40 comprises a core 44 and a shell 42 formed of magnesium. Core 44 contains a second therapeutic agent (e.g., an anti-inflammatory agent) which is different from the first therapeutic agent contained in reservoir layer 54.

A water-permeable barrier layer 52, formed of the same metal as intervening layer 56 (zinc or iron), is disposed over both nanoparticles 40 and intervening layer 56. The magnesium in nanoparticle shells 42 is in direct contact with and more electronegative than the metal (zinc or iron) in barrier layer 52.

Figure 2C:
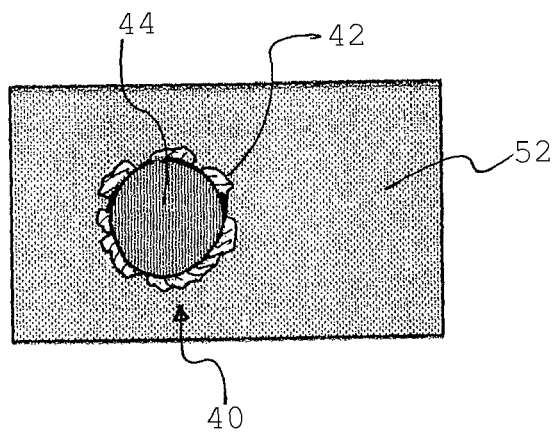

In operation, the stent is implanted into a blood vessel. Body fluids (e.g., blood or plasma) penetrate through barrier layer 52 and come into contact with the metal in nanoparticle shells 42 and the metal in barrier layer 52. Because of the electrolytes in the body fluid, a galvanic current forms between the metal in shell 42 and the metal in barrier layer 52. As seen in FIG. 2C, showing a close-up view of nanoparticle 40 embedded within barrier layer 52, this galvanic current facilitates the erosion of shell 42 of nanoparticle 40, allowing the release of the second therapeutic agent contained in nanoparticle core 44. The second therapeutic agent travels through water-permeable barrier layer 52 and becomes released into the external environment.

Figure 2D:
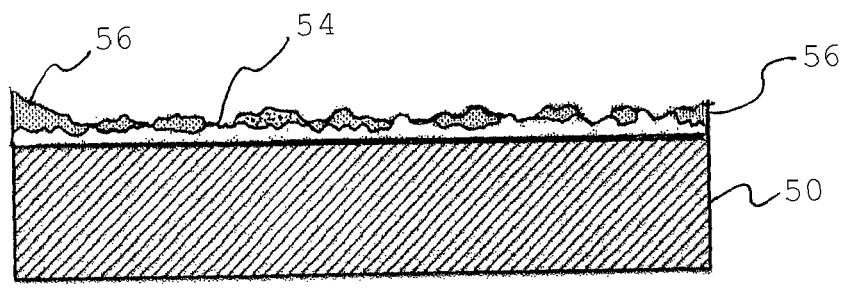

As shown in FIG. 2D, with the further passage of time, both barrier layer 52 and intervening layer 56 undergo erosion by biodegradative or bioresorptive processes. Erosion of barrier layer 52 and intervening layer 56 exposes reservoir layer 54, allowing the release of the first therapeutic agent in reservoir layer 54 into the external environment.

In yet another aspect, the present invention provides a medical device comprising a first reservoir containing a first therapeutic agent. A first barrier layer, comprising a first metal, is disposed over the first reservoir. A second reservoir containing a second therapeutic agent is disposed over the first barrier layer. A second barrier layer, comprising a second metal, is disposed over the second reservoir and the first barrier layer. The second barrier layer is water-permeable, whereas the first barrier layer may be water-permeable or impermeable.

The first and second therapeutic agents may be the same or different. After implantation of the medical device, the first and second barrier layers are designed to undergo erosion to control the release of the first and second therapeutic agents, with the second barrier layer eroding before the first barrier layer erodes.

The first metal (first barrier layer) and the second metal (second barrier layer) are different, with the second metal being less electronegative than the first metal. Also, the first metal in the first barrier layer and the second metal in the second barrier layer are in electrical connectivity; and have an electronegative potential difference that is sufficiently high for a galvanic current to be generated when the medical device is exposed to a physiologic environment (e.g., blood or body fluids containing electrolytes).

As such, when the medical device is exposed to a physiologic environment, the second metal undergoes galvanic corrosion. This galvanic corrosion of the second metal facilitates the erosion of the second barrier layer. In addition to galvanic corrosion, the second barrier layer may also undergo erosion as a result of biodegradative or bioresorptive processes. As the second barrier layer erodes, the second therapeutic agent contained in the second reservoir is released.

Over a longer time frame than the erosion of the second barrier layer, the first barrier layer undergoes erosion through a biodegradation or bioresorption process. As the first barrier layer erodes, the first therapeutic agent contained in the first reservoir is released. The erosion rates of the first and second barrier layers will depend upon various factors, including their composition, thickness, porosity, electrochemical properties, or mechanical properties. As such, these factors can be adjusted to achieve the desired erosion rates of the first and second barrier layers.

In some cases, the second barrier layer is designed to provide a burst release of the second therapeutic agent and the first barrier layer is designed to provide a sustained release of the first therapeutic agent. In some cases, the second barrier layer is designed to erode over a period of less than 2 months; and in some cases, over a period of 2-6 months; and in some cases, over a period of greater than 6 months. In some cases, the first barrier layer is designed to erode over a period of greater than 6 months; and in some cases, over a period of greater than one year.

For example, referring to the embodiment shown in FIGS. 3A-3D, a strut portion 60 of a stent is coated with a first reservoir layer 62 containing a first therapeutic agent. An impermeable inner barrier layer 64, which comprises a first metal, is deposited onto first reservoir layer 62. A second therapeutic agent, provided in a microparticulate formulation as particles 68, is deposited onto inner barrier layer 64. A water-permeable outer barrier layer 66, which comprises a second metal, is deposited onto and around therapeutic agent particles 68. The first metal (inner barrier layer 64) is different from the second metal (outer barrier layer 66), with the second metal having a lesser electronegativity than the first metal. The first metal in inner barrier layer 64 is in direct contact with the second metal in outer barrier layer 66.

Figure 3A:
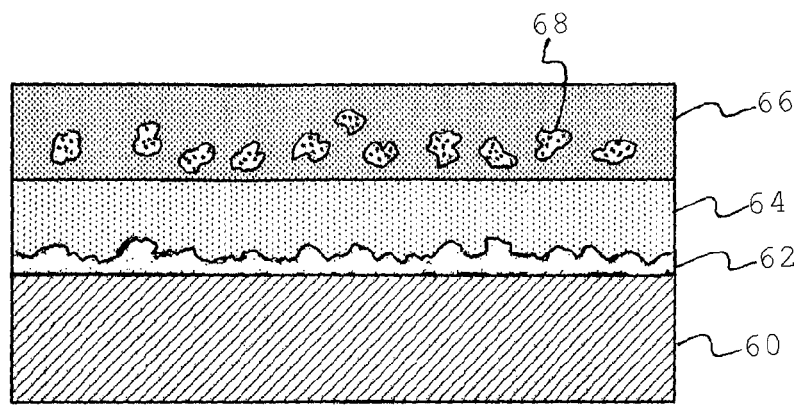
FIGS. 3A-3D show strut portions of a stent according to another embodiment.
Figure 3B:
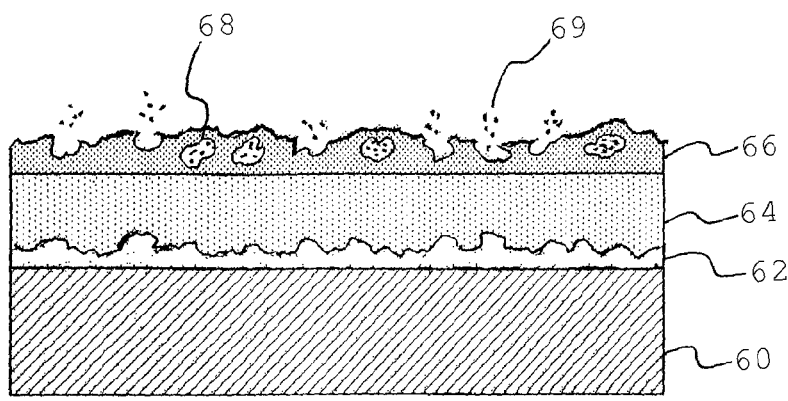
Figure 3C:
Figure 3D:
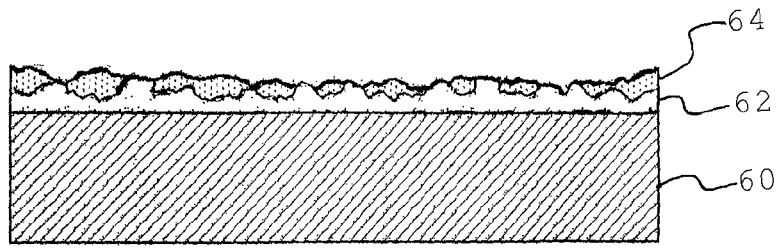

In operation, the stent is implanted into a blood vessel. Body fluids penetrate through outer barrier layer 66 and come into contact with the second metal in outer barrier layer 66 and the first metal in inner barrier layer 64. Because of the electrolytes in the body fluids, a galvanic current forms between the second metal in outer barrier layer 66 and the first metal in inner barrier layer 64. As seen in FIG. 3B, this galvanic current contributes to the erosion of outer barrier layer 66, allowing the release of second therapeutic agent 69 contained in particles 68. FIG. 3C shows strut portion 60 after all of outer barrier layer 66 has eroded. As shown in FIG. 3D, with the further passage of time, inner barrier layer 64 erodes by biodegradative or bioresorptive processes, allowing the release of the first therapeutic agent from first reservoir layer 62.

As mentioned above, the foregoing embodiments can be advantageous in that they provide an initial burst release of a first therapeutic agent, followed by a sustained release of a second therapeutic agent. The first and second therapeutic agents may be the same or different, depending upon the application. For example, in the case of a stent, it may be desirable to provide an initial burst release of a first therapeutic agent to promote blood vessel healing after stent implantation, and then a sustained release of a second therapeutic agent to help prevent thrombosis over a longer period of time.

Non-limiting examples of medical devices that can be used with the present invention include stents, stent grafts, catheters, guide wires, neurovascular aneurysm coils, balloons, filters (e.g., vena cava filters), vascular grafts, intraluminal paving systems, pacemakers, electrodes, leads, defibrillators, joint and bone implants, spinal implants, access ports, intraaortic balloon pumps, heart valves, sutures, artificial hearts, neurological stimulators, cochlear implants, retinal implants, and other devices that can be used in connection with therapeutic coatings. Such medical devices are implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

The therapeutic agents used in the present invention may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaparin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl) ethyleneglycol-N,N,N',N'-tetraacetic acid and mixtures thereof, antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE™; structural protein (e.g., collagen) cross-link breakers such as alagebrium (ALT-711); any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins (MCP-1) and bone morphogenic proteins ("BMP's"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMP's are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin⁻) cells including Lin⁻CD34⁻, Lin⁻CD34⁺, Lin⁻cKit⁺, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells. Any of the therapeutic agents may be combined to the extent such combination is biologically compatible.

The polymeric materials that may be used in the present invention may comprise polymers that are biodegradable or non-biodegradable. Non-limiting examples of suitable non-biodegradable polymers include polystyrene; polystyrene maleic anhydride; block copolymers such as styrene-isobutylene-styrene block copolymers (SIBS) and styrene-ethylene/butylene-styrene (SEBS) block copolymers; polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides including poly(methyl-methacrylate-butylacetate-methylmethacrylate) block copolymers; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butyl acrylate; polyhydroxybutyrate valerate and blends; polycarbonates such as tyrosine-derived polycarbonates and acrylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropyl methyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc calcium phosphate.

The terms "first," "second," and so on, are not intended to suggest a location or ordering of the elements. Rather, the terms are used as labels to facilitate discussion and distinguish elements from one another. The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

What is claimed is:
1. A medical device comprising:
a reservoir containing a first therapeutic agent;
a plurality of nanoparticles disposed over the reservoir, wherein each nanoparticle comprises:
(a) a core containing a second therapeutic agent; and

(b) a shell surrounding the core, wherein the shell comprises a first metal; and a barrier layer disposed over the nanoparticles and the reservoir, wherein the barrier layer comprises a second metal.

2. The medical device of claim 1, wherein the first metal and the second metal are different, and wherein the first metal and the second metal have contrasting electronegativity.

3. The medical device of claim 2, wherein the first metal has a lesser electronegative potential than the second metal.

4. The medical device of claim 3, wherein the first metal undergoes galvanic corrosion when the medical device is exposed to a physiologic environment, and wherein the corrosion of the first metal facilitates erosion of the shell of the nanoparticles.

5. The medical device of claim 4, wherein the barrier layer erodes by biodegradation or bioresorption.

6. The medical device of claim 5, wherein the first therapeutic agent is released as the barrier layer erodes.

7. The medical device of claim 1, wherein the first metal is magnesium and the second metal is iron or zinc.

8. The medical device of claim 1, further comprising an intervening layer disposed between the barrier layer and the reservoir, wherein the intervening layer comprises a third metal.

9. The medical device of claim 8, wherein the nanoparticles are disposed on the intervening layer.

10. The medical device of claim 1, wherein medical device is a vascular stent.

11. The medical device of claim 1 further comprising:

an additional reservoir disposed over the barrier layer, wherein the additional reservoir contains a third therapeutic agent; and an additional barrier layer disposed over the additional reservoir, wherein the additional barrier layer comprises a third metal.

12. The medical device of claim 11, wherein the third metal is different from the second metal, and wherein the third metal has a lesser electronegative potential than the second metal.

13. The medical device of claim 12, wherein the third metal undergoes galvanic corrosion when the medical device is exposed to a physiologic environment, and wherein the corrosion of the third metal facilitates erosion of the additional barrier layer.

14. The medical device of claim 3, wherein the second metal of the barrier layer is in electrical connectivity with the first metal of the nanoparticle shells, and wherein the difference in electronegativities between the first and second metals is sufficient that a galvanic current forms between the first and second metals when the medical device is exposed to a physiologic environment.

* * * * *